(12) United States Patent
Zielinski et al.

(10) Patent No.: US 7,348,010 B2
(45) Date of Patent: Mar. 25, 2008

(54) VACCINE AGAINST CANCER DISEASES THAT ARE ASSOCIATED WITH THE HER-2/NEU ONCOGENE

(76) Inventors: Christoph Zielinski, Dr. Heinrich Maierstrasse 20, Vienna (AT) A-1180; Otto Scheiner, Petersbachgasse 12b, Perchtoldsdorf (AT) A-2380; Erika Jensen-Jarolim, Arbeiterstrandbadstrasse 38, Vienna (AT) A-1210; Heimo Breiteneder, Kandlgasse 9/23, Vienna (AT) A-1070; Hubert Pehamberger, Schwinglgasse 5, Vienna (AT) A-1230

( * ) Notice: Subject to any disclaimer, the term of this patent is extended or adjusted under 35 U.S.C. 154(b) by 414 days.

(21) Appl. No.: 10/469,162

(22) PCT Filed: Feb. 27, 2002

(86) PCT No.: PCT/EP02/02111

§ 371 (c)(1),
(2), (4) Date: Aug. 27, 2003

(87) PCT Pub. No.: WO02/068474

PCT Pub. Date: Sep. 6, 2002

(65) Prior Publication Data

US 2004/0052811 A1    Mar. 18, 2004

(30) Foreign Application Priority Data

Feb. 28, 2001 (EP) .................................. 01104943

(51) Int. Cl.
*C07K 7/08* (2006.01)
*A61K 39/395* (2006.01)
*G01N 33/53* (2006.01)

(52) U.S. Cl. .................. 424/185.1; 530/326; 530/327; 530/402; 530/323; 530/300; 435/7.1; 424/193.1; 436/547

(58) Field of Classification Search .................. None
See application file for complete search history.

(56) References Cited

U.S. PATENT DOCUMENTS

| 5,772,997 A | 6/1998 | Hudziak et al. |
| 5,801,005 A | 9/1998 | Cheever et al. |
| 5,869,445 A | 2/1999 | Cheever et al. |
| 6,610,297 B1 * | 8/2003 | Kricek et al. ............. 424/178.1 |
| 7,060,284 B1 * | 6/2006 | Kaumaya et al. ........ 424/277.1 |

FOREIGN PATENT DOCUMENTS

| JP | 117165 | 5/1993 |
| WO | WO 96/18409 A1 | 6/1996 |
| WO | WO 98/17797 A1 * | 4/1998 |
| WO | WO 9817797 A1 * | 4/1998 |
| WO | WO 99/33969 | 8/1999 |
| WO | WO 99/57981 A1 | 11/1999 |
| WO | WO 01/08636 A2 | 2/2001 |

OTHER PUBLICATIONS

Woodbine, Abstract P442, "Biological Effects of Peptide Antibodies Raised to HER-2/neu. Implications for Therapy of Human Breast Cancer" by Woodbine, et al., The 1997 American Peptide Symposium, Jun. 14-19, 1997, Nashville, Tennessee.*
Perosa et al. (Ann. N.Y. Acad. Sci. 1051: 672-683, 2005.*
Poczatek et al (1999) "Ep-Cam Levels in Prostatic Adenocarcinoma and Prostatic Intraepithelial Neoplasia" *The Journal of Urology*, vol. 162, pp. 1462-1466.
Punt (1998) "New Drugs in the Treatment of Colorectal Carcinoma" *Cancer*, vol. 83, No. 4, pp. 679-689.
Riethmuller et al. (1994) "Randomised trial of monoclonal antibody for adjuvant therapy of resected Dukes' C colorectal carcinoma" *The Lancet*, vol. 343, pp. 1177-1183.
Samonigg et al. (1999) "A Double-Blind Randomized-Phase II Trial Comparing Immunization with Antiidiotype Goat Antibody Vaccine SVC 106 Versus Upspecific Goat Antibodies in Patients with Metastatic Colorectal Cancer" *Journal of Immunotherapy*, vol. 22(6): pp. 481-488.
Stoute et al. (1995) "Induction of Humoral Immune Response against *Plasmodium falciparum* Sporozoites by Immunication with a Synthetic Peptide Mimotope Whose Sequence Was Derived from Screening a Filamentous Phage Epitope Library" *Infection and Immunity*, vol. 63, No. 3 pp. 934-939.
Treon et al. (2000) "Treatment of multiple myeloma by antibody mediated immunotherapy and induction of myeloma selective antigens" *Annals of Oncology* II Supp S107-S111.
Turpen et al. (1995) "Malarial Epitopes Expressed on the Surface of Recombinant Tobacco Mosaic Virus" *Bio/Technology* vol. 13, pp. 53-57.
Zwick, et al. (1998) "Phage-displayed peptide libraries" *Current Opinion in Biotechnology*, vol. 9: pp. 427-436.
Baselga et al. (1988) "Recombinant Humanized Anti-HER2 Antibody (Herceptin) Enhances the Antitumor Activity of Paclitaxel and Doxorubin against HER2/neu Overexpressing Human Breast Cancer Xenografts", Cancer Research 58: 2825-2831.
Baselga, et al. (2000) "Phase I Studies of Anti-Epidermal Growth Factor Receptor Chimeric Antibody C225 Alone and in Combination With Cisplatin", Journal of Clinical Oncology, vol. 18, No. 4, pp. 904-914.

(Continued)

*Primary Examiner*—Christine J. Saoud
*Assistant Examiner*—Nirmal Singh Basi
(74) *Attorney, Agent, or Firm*—Milbank, Tweed, Hadley & McCloy LLP

(57) ABSTRACT

The present invention relates to peptides of the extracellular domain of a HER-2/neu protein, conjugates comprising said peptides linked to an immunogenic carrier, compositions thereof, nucleic acid molecules, vectors and transformed or transfected host cells comprising said nucleic acid molecules encoding said peptides or conjugates, and methods for producing the disclosed peptides, conjugates and compositions. The present invention also relates to diagnostic methods of detecting cancerous conditions associated with HER-2/neu or monitoring the effectiveness of treatment against cancerous conditions associated with HER-2/neu. The present invention also relates to methods of eliciting or enhancing an immune response to HER-2/neu in a subject in need thereof.

10 Claims, 2 Drawing Sheets

OTHER PUBLICATIONS

Behr et al. (1999) "Low-versus High-Dose Radioimmunotherapy with Humanized Anti-CD22 or Chimerica Anti-CD20 Antibodies in a Broad Spectrum of B Cell-associated Malignancies", Clinical Cancer Research vol. 5, 3304s-3314s.

Braun et al. (1999) "Monoclonal Antibody Therapy with Edrecolomab in Breast Cancer Patients: Monitoring of Elimination of Disseminated Cytokeratin-positive Tumor Cells in Bone Marrow", Clinical Canser Research vol. 5, 3999-4004.

Cha et al. (1996) "Random phage mimotopes recognized by monoclonal antibodies against the pyruvate dehydrogenase complex-X2 (PDC-E2)", Proc. Natl. Acad. Sci. USA, vol. 93, pp. 10949-10954 Immunology.

D'Mello et al. (1997) "Definition of the Primary Structure of Hepatitis B Virus (HBV) pre-S Hepatocyte Binding Domain Using Random Peptide Libraries", VIROLOGY vol. 237, pp. 319-326.

Huang et al. (1999) "Epidermal Growth Factor Receptor Blockade with C225 Modulates Proliferation, Apoptosis, and Radiosensitivity in Squamous Cell Carcinomas of the Head and Neck", Cancer Research vol. 59, pp. 1935-1940.

Martin, et al. (1999) "Expression of the 17-1A antigen in gastric and gastro-oesophageal junction adenocarcinomas: a potential immunotherapeutic target?" J. Clin. Pathol, vol. 52, pp. 701-704.

McCormick et al. (1999) "Rapid production of specific vaccines for lymphoma by expression of the tumor-derived single-chain Fv Epitopes in tobacco plants", Proc. Natl. Acad. Sci. USA vol. 96, pp. 703-708 Medical Sciences.

Milpied, et al. (2000) "Humanized anti-CD20 monoclonal antibody (Rituximab) in post transplant B-lymphoproliferative disorder: A retrospective analysis on 32 patients", Annals of Oncology II Suppl.S113-S116 Kluwer Academic Publishers.

Orlandi et al. (1994) "Antigenic and Immunogenic mimicry of the HER2/neu oncoprotein by phage-displayed peptides", Eur. J. Immunol. vol. 24, pp. 2868-2873.

Poczatek et al. (1999) "Ep-Cam Levels in Prostatic Adenocarcinoma and Prostatic Intraepithelial Neoplasia", The Journal of Urology, vol. 162, pp. 1462-1466.

Punt (1998) "New Drugs in the Treatment of Colorectal Carcinoma", CANCER, vol. 83, No. 4, pp. 679-689.

Turpen et al. (1995) "Malaria Epitopes Expressed on the Surface of Recombinant Tobacco Mosaic Virus", Bio/Technology vol. 13, pp. 53-57.

Zwick, et al. (1998) "Phage-displayed peptide libraries", Current Opinion in Biotechnology, vol. 9: pp. 427-436.

Mittelman, Abraham et al., "Human high molecular weight melanoma-associated antigen (HMV-MAA) mimicry by mouse anti-idiotypic monoclonal antibody MK2-23: Induction of humoral anti-HMV-MAA immunity and prolongation of survival in patients with stage IV melanoma," Proc. Natl. Acad. Sci. USA, vol. 89, pp. 446-470, Jan. 1992.

Mittelman, A. et al., "Active Specific Immunotherapy in Patients with Melanoma. A Clinical Trial with Mouse Antiidiotypic Monoclonal Antibodies Elicited with Syngeneic Anti-High-Molecular-Weight-Melanoma-Associated Antigen Monoclonal Antibodies," J. Clin. Invest. Dec. 1990, 86, 2136-2144.

Geiser, Martin et al., "Identification of the Human Melanoma-associated Chondroitin Sulfate Proteoglycan Antigen Epitope Recognized by the Antitumor Monoclonal Antibody 763.74 from a Peptide Phage Library," Cancer Research 59, 905-910, Feb. 15, 1999.

Mittelman, Abraham et al., "Human High Molecular Weight-Melanoma Associated Antigen Mimicry by Mouse Anti-Idiotypic Monoclonal Antibody MK2-23: Modulation of the Immunogenicity in Patients with Malignant Melanoma," Clinical Cancer Research vol. 1, 705-173, Jul. 1995.

Ziai, M. Reza et al., "Analysis with Monoclonal Antibodies of the Molecular and Cellular Heterogeneity of Human High Molecular Weight Melanoma Associated Antigen," Cancer Research 47, 2474-2480, May 1, 1987.

Price, Michael et al., "Enhancement of Cell-mediated Immunity in Melanoma Patients Immunized with Murine Anti-Idiotypic Monoclonal Antibodies (MELIMMUNE) That Mimic the High Molecular Weight Proteoglycan Antigen," Clinical Cancer Research vol. 4, 2363-2370 Oct. 1998.

Ferrone, S. et al., "Active Specific Immunotherapy of Malignant Melanoma and Peptide Mimics of the Human High-Molecular-Weight Melanoma-Associated Antigen," Recent Results Cancer Res., 2001. 158, 231-5).

Wison, Barry S. et al., Distribution and Molecular Characterization of a Cell-Surface and a Cytoplasmic Antigen Detectable in Human Melanoma Cells with Monoclonal Antibodies, Int. J. Cancer: 28, 293-300 (1981).

Leitner, Agnes et al., "A mimotope defined by phage display inhibits IgE binding to the plant panallergen profilin," Eur. J. Immunol. 1998, 28:2921-2927.

* cited by examiner

Western blot: Immunoprecipitation of lysate of SKB-3 cells with mouse Sera

Her-2/neu at 185 kDa

Lane 1: Buffer control

Lane 2 - 4: Control mice

Lane 5 - 9: Mice immunized with sequence 1 + sequence 2

VACCINE AGAINST CANCER DISEASES THAT ARE ASSOCIATED WITH THE HER-2/NEU ONCOGENE

FIELD OF INVENTION

The present invention relates to peptides of the extracellular domain of a HER-2/neu protein that are useful in compositions, comprising the peptide or the peptide conjugated to an immunogenic carrier that can elicit or enhance an immune response in a subject. The present invention also relates to methods for the diagnosis and monitoring of the treatment of HER-2/neu-associated oncogenic conditions.

BACKGROUND OF INVENTION

In recent years, Western industrial nations have seen a steady increase in cancerous diseases, which have become one of the leading causes of death. For example, breast cancer is the most widespread cancer in women, affecting about 10% of all women in Western industrial nations.

Hitherto known methods for treating cancerous diseases aim primarily at early recognition of the disease and surgical methods or preferably selective destruction of tumor cells by chemo- or radiotherapy. These methods, however, do not permit any effective prophylaxis against the genesis of the cancerous diseases and also involve very considerable side effects.

It is further known that many kinds of cancer, including breast, ovarian, colon, lung and prostate cancer, involve an overexpression of HER-2/neu protein (also known as p185 or c-erbB2)—the protein product of the HER-2/neu oncogene. HER-2/neu protein is closely associated with a malignant and aggressive cancer phenotype. HER-2/neu protein is a transmembrane protein with a relative molecular mass of 185 kD and has a length of approximately 1255 amino acids. The amino acid sequence of HER-2/neu protein and the nucleic acid sequence of a DNA sequence encoding the HER-2/neu protein are disclosed in U.S. Pat. No. 5,869,445, which is incorporated herein by reference. The extracellular domain of HER-2/neu protein includes the peptide sequence from amino acid 1 to amino acid 675.

U.S. Pat. No. 5,869,445 discloses a method for stimulating an immune response to HER-2/neu protein in which a polypeptide having the sequence from amino acid 676 to 1255 of HER-2/neu protein is administered.

The invention is based on the finding that a vaccine comprising portions of the extracellular domain of HER-2/neu protein or functionally equivalent peptides thereof as effective components, can avoid the disadvantages of conventional cancer treatments, provide effective prophylaxis, and offer alternative to the methods of U.S. Pat. No. 5,869,445. The inventive peptides, functionally equivalent peptides thereof, conjugates and compositions permit active immunization against cancerous diseases associated with the HER-2/neu oncogene, thereby permitting prophylaxis against these cancerous diseases. In addition, the inventive peptides, functionally equivalent peptides thereof, conjugates and compositions can be used to treat an already existing cancerous disease or to accompany conventional cancer treatments. Application of the inventive peptides, functionally equivalent peptides thereof, conjugates and compositions can completely or partly avoid the considerable disadvantages associated with conventional cancer treatments.

SUMMARY OF INVENTION

The present invention relates to a peptide consisting of between 9 to 25 contiguous amino acids of the extracellular domain of a HER-2/neu protein. In another embodiment, the peptide of the present invention consists of between 10 to 20 contiguous amino acids of the extracellular domain of a HER-2/neu protein. Preferably, the peptides of the present invention consists of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the peptides of the present invention consist of a sequence of amino acids corresponding to amino acid positions 544 to 560 of SEQ ID NO: 3 or a sequence of amino acids corresponding to amino acid positions 610 to 623 of SEQ ID NO: 3. Most preferably, the peptides of the present invention consist of the amino acid sequence CRVLQGLPREYVNARHC (SEQ ID NO: 1) or the amino acid sequence YMPIWKFPDEEGAC (SEQ ID NO: 2).

In one embodiment, the peptides of the present invention further bind antibodies that specifically bind a HER-2/neu protein. In another embodiment, the peptides of the present invention elicit or enhance an immune response. The present invention also provides compositions comprising the peptides of the present invention and a pharmaceutically acceptable carrier.

The present invention provides kits for detecting antibodies that specifically bind a HER-2/neu protein, wherein said kit comprises a first container or containers comprising any peptide of the present invention, or a functionally equivalent peptide thereof, and a second container containing buffers and factors necessary to form or detect a complex between a HER-2/neu protein and a peptide or functionally equivalent peptide thereof.

The present invention also provides functionally equivalent peptides of any of the peptides of the present invention. In one embodiment, the present invention provides functionally equivalent peptides of a peptide consisting of between 9 to 25 contiguous amino acids of the extracellular domain of a HER-2/neu protein. In another embodiment, the present invention provides functionally equivalent peptides of a peptide consisting of between 10 to 20 amino acids of the extracellular domain of a HER-2/neu protein. Preferably, the present invention provides functionally equivalent peptides of a peptide consisting of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the present invention provides functionally equivalent peptides of a peptide consisting of a sequence of amino acids corresponding to amino acid positions 544 to 560 of SEQ ID NO: 3 or a sequence of amino acids corresponding to amino acid positions 610 to 623 of SEQ ID NO: 3. Most preferably, the present invention provides functionally equivalent peptides of a peptide consisting of the amino acid sequence CRVLQGLPREYVNARHC (SEQ ID NO: 1) or the amino acid sequence YMPIWKFPDEEGAC (SEQ ID NO: 2).

In one embodiment, the functionally equivalent peptides of the present invention are produced by: 1) the insertion of one or more amino acids to any peptide of the present invention; 2) the deletion of one or more amino acids to any peptide of the present invention; 3) the substitution of amino acids with non-identical amino acids or non-amino acids within any peptide of the present invention; or 4) the modification of one or more amino acids of any peptide of the present invention by adding carbohydrate, lipid, phosphate groups, acetyl groups, and the like. Preferably, the functionally equivalent peptides of the present invention are produced by the substitution of one or more amino acids of the peptides of the present invention by non-identical amino acids or non-amino acids. More preferably, the functionally equivalent peptides of the present invention are produced by the conservative substitution of one or more amino acids of the peptides of the present invention. More preferably, the functionally equivalent peptides of the present invention are produced by introducing between 1 and 5 conservative substitutions. In another preferred embodiment, the functionally equivalent peptides of the present invention are produced by introducing between 1 and 3 conservative substitutions. Most preferably, the functionally equivalent peptides of the present invention are produced by introducing one conservative substitution.

The present invention also contemplates functionally equivalent peptides wherein, in addition to the conservative substitutions disclosed herein, one or more of the amino acids of the peptide are modified by oxidation or reduction.

The present invention also contemplates functionally equivalent peptides wherein, in addition to the conservative substitutions disclosed herein, one or more of the amino acids of the peptides of the present invention are modified by the addition of one or more members selected from a group consisting of: carbohydrate, lipid, phosphate groups and acetyl groups.

The present invention also contemplates functionally equivalent peptides wherein, in addition to the insertions, deletions and substitutions disclosed herein, one or more of the amino acids of the peptides of the present invention are modified by oxidation or reduction. In a preferred embodiment, the present invention contemplates functionally equivalent peptides wherein one or more of the amino acids of any of the peptides disclosed herein are modified by oxidation or reduction.

The present invention also contemplates functionally equivalent peptides wherein, in addition to the insertions, deletions and substitutions disclosed herein, one or more of the amino acids of any of the peptides disclosed herein are modified by the addition of one or more members selected from a group consisting of: carbohydrate, lipid, phosphate groups and acetyl groups. In a preferred embodiment, the present invention also provides functionally equivalent peptides of any of the peptides disclosed herein, wherein one or more of the amino acids of the peptide are modified by the addition of one or more members selected from a group consisting of: carbohydrate, lipid, phosphate groups and acetyl groups.

In one embodiment, the functionally equivalent peptides of the present invention further bind antibodies that specifically bind a HER-2/neu protein.

In one embodiment, the functionally equivalent peptides of the present invention elicit or enhance an immune response. In a preferred embodiment, the ability of the functionally equivalent peptides of the present invention to elicit or enhance an immune response is substantially equivalent to that of the corresponding, unmodified peptide.

In another embodiment, the functionally equivalent peptides of the present invention elicit or enhance an immune response when the functionally equivalent peptide is conjugated to an immunogenic carrier. In a preferred embodiment, the ability of the functionally equivalent peptides of the present invention to elicit or enhance an immune response when the functionally equivalent peptide is conjugated to an immunogenic carrier is substantially equivalent to that of the corresponding, unmodified peptide.

The present invention is further directed to peptides, and functionally equivalent peptides thereof, linked to an immunogenic carrier to form a conjugate that elicits or enhances an immune response to a HER-2/neu protein in a subject in need thereof. In a preferred embodiment, the peptides of said conjugates consist of between 9 to 25 contiguous amino acids of the extracellular domain of a HER-2/neu protein. In another embodiment, the peptides of said conjugates consists of between 10 to 20 amino acids. Preferably, the peptides of said conjugates consist of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the peptides of the conjugates of the present invention consist of a sequence of amino acids corresponding to amino acid positions 544 to 560 of SEQ ID NO: 3 or a sequence of amino acids corresponding to amino acid positions 610 to 623 of SEQ ID NO: 3. Most preferably, the conjugates of the present invention comprise peptides that consist of the amino acid sequence CRVLQGLPREYVNARHC (SEQ ID NO: 1) or the amino acid sequence YMPIWKFPDEEGAC (SEQ ID NO: 2).

The immunogenic carrier of the conjugates of the present invention is selected from a group of compounds, well known in the art, that, when linked to a peptide of the present invention, elicits or enhances an immune response to a HER-2/neu protein in a subject in need thereof. Preferably, the immunogenic carrier is selected from the group consisting of key-hole limpet hemocyanin (KLH) and tetanus toxoid (TT).

In a preferred embodiment, the conjugates of the present invention comprise between 2 and 10 peptides of the present invention linked to an immunogenic carrier. Preferably, the present invention contemplates conjugates comprising 5 peptides linked to an immunogenic carrier. More preferably, the present invention contemplates conjugates comprising 3 peptides linked to an immunogenic carrier. Most preferably, the conjugates of the claimed invention comprise 2 peptides linked to an immunogenic carrier. The present invention contemplates conjugates wherein each of the peptides may be linked directly to the immunogenic carrier. Alternatively, a peptide or peptides of the conjugates of the present invention may form links to one or more of the other peptides of the conjugate, wherein one or more of those peptides are linked to the immunogenic carrier. The peptides of the conjugates of the present invention may be either identical or non-identical.

The present invention also provides compositions comprising any of the disclosed conjugates and a pharmaceutically acceptable carrier, wherein the compositions elicit or enhance an immune response. In a preferred embodiment, the compositions of the present invention comprise conjugates wherein the peptides consist of between 9 to 25 contiguous amino acids of the extracellular domain of a HER-2/neu protein. In another embodiment, the compositions comprise conjugates wherein the peptides consist of between 10 to 20 amino acids. Preferably, the compositions comprise conjugates wherein the peptides consist of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the compositions of the present invention comprise conjugates wherein the peptides consist of a sequence of amino acids corresponding to amino acid positions 544 to 560 of SEQ ID NO: 3 or a sequence of amino acids corresponding to amino acid positions 610 to 623 of SEQ ID NO: 3. Most preferably, the compositions comprise conjugates wherein the peptides consist of the amino acid sequence CRVLQGLPREYVNARHC (SEQ ID NO: 1) or the amino acid sequence YMPIWKFPDEEGAC (SEQ ID NO: 2). The present invention also contemplates methods of eliciting or enhancing an immune response comprising the administration of said compositions to a subject in need thereof.

The present invention also provides isolated nucleic acid molecules that encode the disclosed peptides of the present invention and functionally equivalent peptides thereof. In one embodiment, the present invention provides an isolated nucleic acid molecule encoding a peptide consisting of between 9 to 25 contiguous amino acids of the extracellular domain of a HER-2/neu protein. In another embodiment, the isolated nucleic acid molecules of the present invention encode a peptide consisting of between 10 to 20 contiguous amino acids of the extracellular domain of a HER-2/neu protein. Preferably, the nucleic acid molecules of the present invention encode a peptide consisting of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the nucleic acid molecules of the present invention encode a peptide consisting of a sequence of amino acids corresponding to amino acid positions 544 to 560 of SEQ ID NO: 3 or a sequence of amino acids corresponding to amino acid positions 610 to 623 of SEQ ID NO: 3. Most preferably, the nucleic acids of the present invention encode a peptide that consists of the amino acid sequence CRVLQGLPREYVNARHC (SEQ ID NO: 1) or the amino acid sequence YMPIWKFPDEEGAC (SEQ ID NO: 2).

The present invention also contemplates an isolated nucleic acid molecule that, in addition to encoding one or more of the peptides and/or functionally equivalent peptides of the present invention, further encodes an immunogenic carrier. In a preferred embodiment, the isolated nucleic acid molecules encode one or more of the peptides and/or functionally equivalent peptides of the present invention and an immunogenic carrier selected from the group consisting of key-hole limpet hemocyanin (KLH) and tetanus toxoid (TT).

The present invention also provides a DNA vector comprising an isolated nucleic acid molecule of the present invention, as described, that is operably linked to one or more suitable regulatory sequences which induce expression and/or integration of the DNA sequence in a host cell. In a preferred embodiment, the vectors of the present invention comprise an isolated nucleic acid molecule encoding a peptide consisting of between 9 to 25 contiguous amino acids of the extracellular domain of a HER-2/neu protein. In another embodiment, the vectors of the present invention comprise isolated nucleic acid molecules that encode a peptide consisting of between 10 to 20 contiguous amino acids of the extracellular domain of a HER-2/neu protein. Preferably, the vectors of the present invention comprise an isolated nucleic acid molecule that encodes a peptide consisting of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the vectors of the present invention comprise an isolated nucleic acid molecule that encodes a peptide consisting of a sequence of amino acids corresponding to amino acid positions 544 to 560 of SEQ ID NO: 3 or a sequence of amino acids corresponding to amino acid positions 610 to 623 of SEQ ID NO: 3. Most preferably, the vectors of the present invention comprises an isolated nucleic acid molecule that encodes a peptide consisting of the amino acid sequence CRVLQGLPREYVNARHC (SEQ ID NO: 1) or the amino acid sequence YMPIWKFPDEEGAC (SEQ ID NO: 2).

In one embodiment, the isolated nucleic acid molecules and vectors of the present invention encode peptides that further bind antibodies that specifically bind a HER-2/neu protein.

The present invention also provides host cells transformed or transfected with a vector comprising an isolated nucleic acid molecule of the present invention operably linked to one or more suitable regulatory sequences which induce expression and/or integration of the DNA sequence in a host cell. In a preferred embodiment, the host cells of the present invention are transformed or transfected with vectors comprising an isolated nucleic acid molecule encoding a peptide consisting of between 9 to 25 contiguous amino acids of the extracellular domain of a HER-2/neu protein. In another embodiment, the host cells of the present invention are transformed or transfected with vectors comprising isolated nucleic acid molecules that encode a peptide consisting of between 10 to 20 contiguous amino acids of the extracellular domain of a HER-2/neu protein. Preferably, the host cells of the present invention are transformed or transfected with vectors comprising an isolated nucleic acid molecule that encodes a peptide consisting of between 9 to 25 contiguous amino acids of the extracellular domain of a HER-2/neu protein, wherein the extracellular domain of the HER-2/neu protein is described by amino acids corresponding to amino acid positions 1-675 of SEQ ID NO: 3. More preferably, the host cells of the present invention are transformed or transfected with vectors comprising an isolated nucleic acid molecule that encodes a peptide consisting of a sequence of amino acids corresponding to amino acid positions 544 to 560 of SEQ ID NO: 3 or a sequence of amino acids corresponding to amino acid positions 610 to 623 of SEQ ID NO: 3. Most preferably, the host cells of the present invention are transformed or transfected with vectors comprising an isolated nucleic acid molecule that encodes a peptide consisting of the amino acid sequence CRVLQGLPREYVNARHC (SEQ ID NO: 1) or the amino acid sequence YMPIWKFPDEEGAC (SEQ ID NO: 2).

The present invention also provides methods of eliciting or enhancing an immune response in a subject in need thereof comprising administering any of the compositions of the present invention wherein the composition elicits or enhances an immune response in said subject.

The present invention also provides methods of eliciting or enhancing an immune response in a subject in need thereof comprising administering a composition comprising any of the transformed or transfected host cells described above wherein the composition elicits or enhances an immune response in said subject.

The present invention also provides methods of producing a peptide of the present invention or functionally equivalent peptide thereof comprising culturing any of the host cells of the present invention. In a preferred embodiment, the method of producing a peptide of the present invention or functionally equivalent peptide thereof further comprises purification of said peptide.

The present invention also provides methods of producing a conjugate comprising culturing the host cells described above, wherein the host cells are transformed or transfected with a vector comprising an isolated nucleic acid molecule encoding any one or more of the peptides of the present invention or functionally equivalent peptides thereof, as described above, and that further encodes an immunogenic carrier. In a preferred embodiment, the method of producing a peptide of the present invention or functionally equivalent peptide thereof further comprises purification of said peptide.

The present invention also provides methods of producing a conjugate comprising linking any one or more of the peptides of the present invention or functionally equivalent peptides thereof to an immunogenic carrier.

The present invention also provides methods of detecting the presence of antibodies against the HER-2/neu protein comprising mixing a biological fluid or tissue obtained from a subject with any of the peptides of the present invention or functionally equivalent peptides thereof for a complex between said peptide and said antibody, wherein complex formation indicates the presence of antibodies against a HER-2/neu protein.

DETAILED DESCRIPTION OF INVENTION

Figure 1:
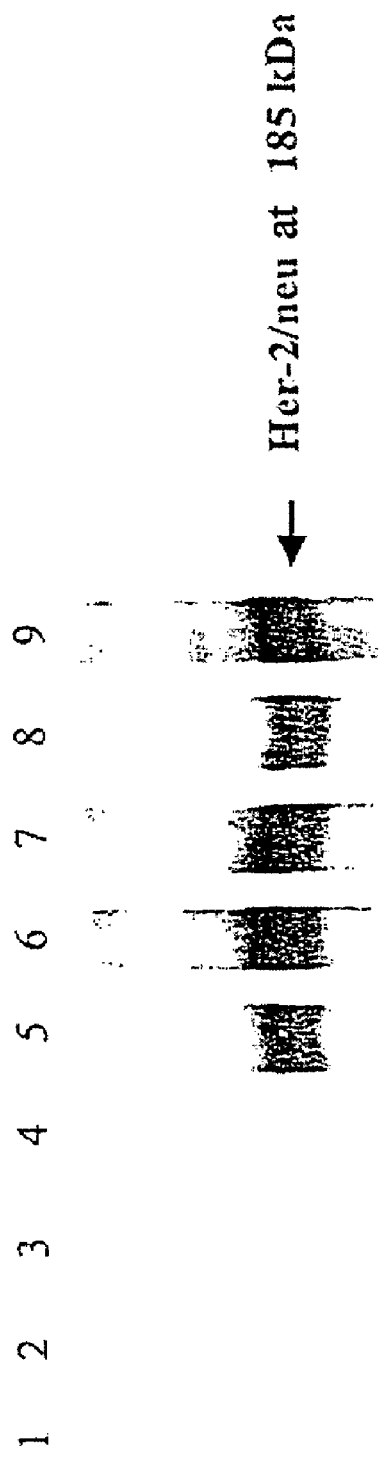
FIG. 1 depicts a Western blot of the immunoprecipitation of a lysate of SKBR-3 cells overexpressing HER-2/neu with sera of mice treated with the inventive peptides and untreated mice for detecting the immune response after administration of the peptides. Lane 1: Buffer control; Lanes 2-4: control mouse sera; Lanes 5-9: mice immunized with peptides described by SEQ ID NO: 1 and 2.
Figure 2:
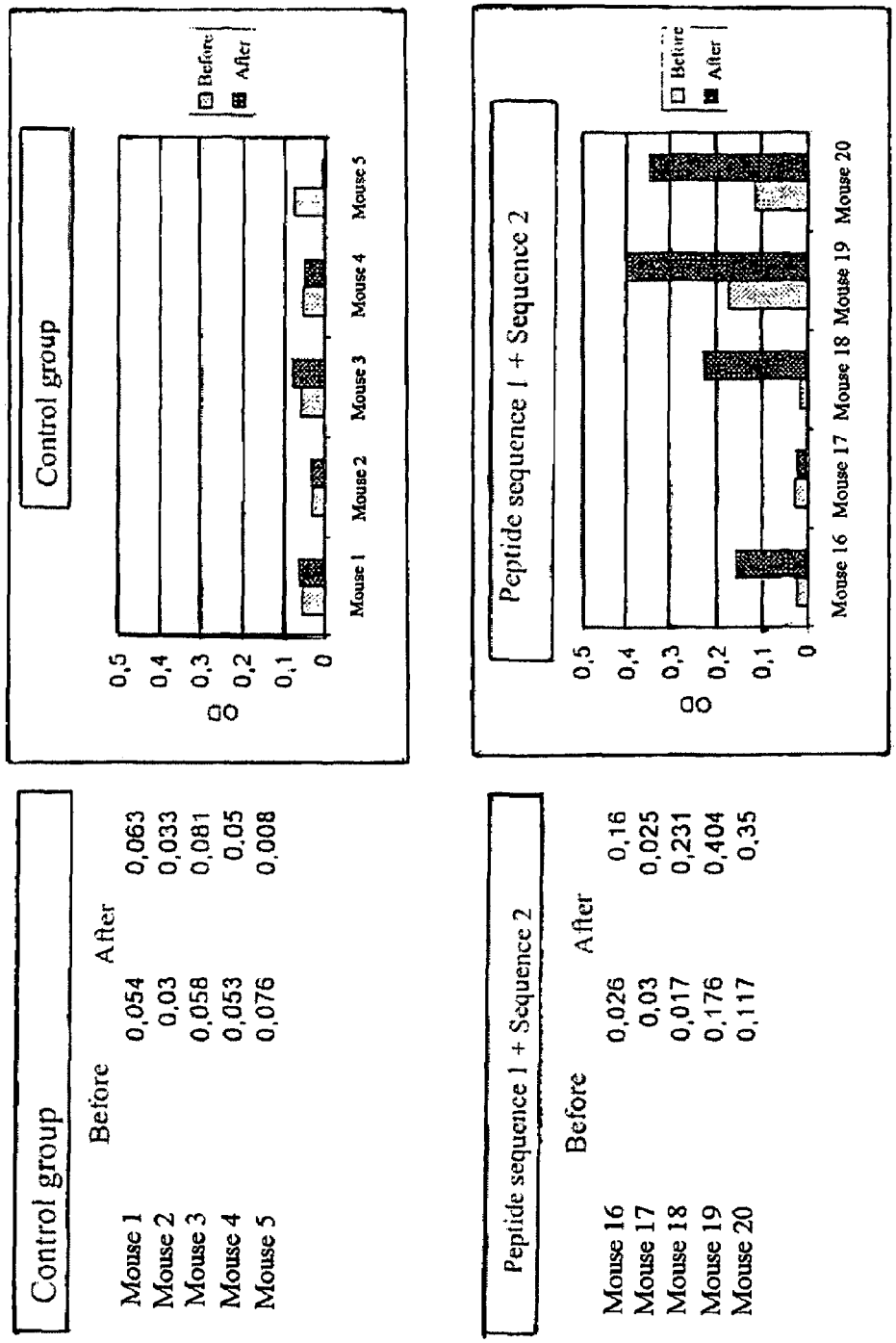
FIG. 2 depicts ELISA data of the sera of mice treated with the inventive peptides and untreated mice for detecting the immune response after administration of the peptides.

As used herein, "biological fluids" refers to any fluid in or isolated from human or other animal, including but not limited to, whole blood, serum, plasma, ascites, cerebrospinal fluid, urine, lymph fluids, synovial fluids, bronchoalveolar lavage, pleural fluids, various external secretions of the respiratory, intestinal and genitourinary tracts, tears, saliva, milk, white blood cells, myelomas, normal and diseased cells, cell culture supernatants, fixed tissue specimens and fixed cell specimens, and the like.

As used herein, the term "conjugate" refers to a chemical compound that has been formed by the joining of two or more molecules.

As used herein, the term "elicit or enhance an immune response" refers to the ability of an agent to act as an antigen and produce antibodies specific to the agent, or the ability of an agent to cause T cells to proliferate, differentiate, produce cytolytic activity or induce cytokine production.

As used herein, the term "extracellular domain of a HER-2/neu" refers to the portion of the HER-2/neu protein that is located outside the cell, or a fragment thereof. Preferably, the "extracellular domain of a HER-2/neu" consists of amino acids 1-675 of the polypeptide described by SEQ ID NO: 3.

As used herein, the term "immunogenic" refers to the ability of a molecule or composition to induce a humoral or cellular immune response.

As used herein, the term "isolated peptide" refers to a peptide after physical, mechanical or chemical methods are employed to remove the peptide from cellular constituents that are normally associated with the recombinantly produced peptide. A skilled artisan can readily employ standard purification methods to obtain such an isolated peptide.

As used herein, the term "linked" refers to a covalent association between an immunogenic carrier and one or more peptides of the claimed invention. For example, the covalent association may be either a peptide or a non-peptide bond. Linking of a peptide or peptides to an immunogenic carrier through a peptide bond may be accomplished recombinantly by methods well known in the art. Non-peptide covalent associations may be prepared through reaction of particular functional groups of amino acid side chains or the N- and/or C-terminals of the peptide(s) or carrier to form a covalent bond. The functional groups may be either naturally present in the peptide(s) or immunogenic carrier or introduced by chemical modification of the peptide(s) and/or immunogenic carrier by methods well known in the art.

As used herein, the term "recombinantly produced" refers to material produced by genetic engineering. As used herein, the term "recombinant DNA" refers to genetically engineered DNA prepared by transplanting or splicing genes from one species into the cells of a host organism of the same or a different species for purposes of replication, amplification, integration, or expression.

As used herein, the term "functionally equivalent peptide" refers to a peptide of between 9 and 25 amino acids, wherein any one or more of the following modifications have been made: 1) one or more amino acids of a peptide are replaced by other non-identical amino acids or non-amino acids; 2) amino acids are deleted; 3) amino acids are added to the peptide; or 4) amino acids are chemically or post-translationally modified by oxidation, reduction, condensation, and the addition of chemical groups such as carbohydrates, lipids, phosphates, acetyl groups, and the like.

Amino acid substitutions may be made in a variety of ways to provide the functionally equivalent peptides of the present invention. First, an amino acid may be conservatively substituted by replacing an amino acid with one that has similar charge, steric, hydropathic or chemical properties. The following groups contain amino acids that share similar charge, steric, hydropathic or chemical properties: (1) Ala (A), Gly (G), Glu (E), Asp (D), Gln (Q), Asn (N), Ser (S), Thr (T); (2) Cys (C), Ser (S), Tyr (Y), Thr (T); (3) Val (V), Ile (I), Leu (L), Met (M), Ala (A), Phe (F); (4) Lys (K), Arg (R), His (H); and (5) Phe (F), Tyr (Y), Trp (W), His (H). Substitution of an amino acid with a member of the same group would represent a conservative substitution. Substitution of an amino acid of one group with an amino acid from another group represents a non-conservative substitution.

The above-described sequence modifications may be introduced using standard recombinant techniques or by automated synthesis of the modified peptide. Oligonucleotide-directed site-specific mutagenesis procedures can be employed to provide a gene in which particular codons are altered to produce the desired substitution, deletion, or insertion. Exemplary methods of making the alterations set forth above are disclosed by Walder et al. (1986) *Gene* 42: 133; Bauer et al. (1985) *Gene* 37: 73; Craik (1985) *BioTechniques* January, 1985: 12-19; Smith et al. (1981) *Genetic Engineering: Principles and Methods*, Plenum Press; and U.S. Pat. Nos. 4,518,584 and 4,737,462.

Functionally equivalent peptides of the present invention may be produced by identifying and replacing amino acids in T-cell motifs that have the potential to bind to class II MHC molecules (for CD4+ T-cell response) or class I MHC molecules (for CD8+ T-cell response). Peptides of the extracellular domain of a HER-2/neu protein containing a motif with theoretical potential to bind to class II MHC molecules may be identified by computer analysis. For example, a protein sequence analysis package, "T Sites", incorporates several computer algorithms designed to distinguish potential sites for T-cell recognition. (Feller et al. (1991) *Nature* 349: 720-721). Two searching algorithms—AMPHI (Feller et al. (1991) *Nature* 349: 720-721; Margalit et al. (1987) *J. Immunol.* 138: 2213-2229) and the Rothbard and Taylor algorithm (Rothbard et al. (1988) *EMBO* 7: 93-100)—identify epitope motifs according to alpha-helical periodicity and amphipathicity and epitope motifs according to charge and polarity, respectively. Peptides with both motifs are most appropriate for binding to class II MHC molecules. CD8+-T cells recognize peptide bound to class I MHC molecules. Falk et al. have determined that peptides binding to particular MHC molecules share discernible sequence motifs (Falk et al. (1991) *Nature* 351: 290-296).

Functionally equivalent peptides of the present invention can be produced, for example, by using bacteriophage peptide-expression libraries of structural variants of the peptides of present invention. The libraries are initially screened to identify those peptides that bind an antibody that specifically binds either the corresponding unmodified peptide or a HER-2/neu protein. Peptides identified in this initial screening are then screened to determine whether they elicit or enhance an immune response. A similar procedure for producing such functionally equivalent peptides is described in European Patent Application EP 100 41 342.0, the disclosure of which is incorporated herein by reference.

Functionally equivalent peptides may be assayed to determine whether they retain the ability to elicit or enhance an immune response by contacting T cells with the structurally-modified peptide and assaying the response. It will be evident to those of ordinary skill in the art that peptides and functionally equivalent peptides may be tested for the ability to elicit or enhance an immune response by a variety of assays that are well known in the art, including detection of: 1) T-cell proliferation; 2) T-cell differentiation; 3) cytokine production; and 4) cytolytic activity.

Bacteriophage peptide-expression libraries may generally be produced and screened using methods known to those of ordinary skill in the art, such as methods described in Sambrook et al. (1989) *Molecular Cloning: A Laboratory Manual*, Cold Spring Harbor Laboratories, Cold Spring Harbor, N.Y., which is incorporated herein by reference. In the context of this invention, a "detection reagent" is any compound capable of binding to HER-2/neu protein, which may then be detected by any means known to those of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenz-thiazoline sulfonic acid. Plaques containing nucleic acid sequences that express functionally equivalent peptides of the present invention are isolated and purified by techniques known to those of ordinary skill in the art. Appropriate methods may be found, for example, in Sambrook et al., *Molecular Cloning: A Laboratory Manual*, Cold Spring Harbor Laboratories, Cold Spring Harbor, N.Y., 1989.

In one embodiment, the peptide libraries used in the present invention may be libraries that are chemically synthesized in vitro. Examples of such libraries are given in Houghten et al. (1991) *Nature* 354: 84-86, which describes mixtures of free hexapeptides in which the first and second residues in each peptide were individually and specifically defined; Lam et al. (1991) *Nature* 354: 82-84, which describes a "one bead, one peptide" approach in which a solid phase split synthesis scheme produced a library of peptides in which each bead in the collection had immobilized thereon a single, random sequence of amino acid residues; Medynski (1994) *Bio/Technology* 12: 709-710, which describes split synthesis and T-bag synthesis methods; and Gallop et al. (1994) *J. Medicinal Chemistry* 37(9): 1233-1251. Simply by way of other examples, a combinatorial library may be prepared, according to the methods of Ohlmeyer et al. (1993) *Proc. Natl. Acad. Sci. USA* 90: 10922-10926; Erb et al. (1994) *Proc. Natl. Acad. Sci. USA* 91: 11422-11426; Houghten et al. (1992) *Biotechniques* 13: 412; Jayawickreme et al. (1994) *Proc. Natl. Acad. Sci. USA* 91: 1614-1618; or Salmon et al. (1993) *Proc. Natl. Acad. Sci. USA* 90: 11708-11712. PCT Publication No. WO 93/20242 and Brenner et al. (1992) *Proc. Natl. Acad. Sci. USA* 89: 5381-5383 describe "encoded combinatorial chemical libraries," that contain oligonucleotide identifiers for each chemical polymer library member. Compounds synthesized so as to be immobilized on a substrate are released from the substrate prior to use in the inhibition assay.

Libraries of non-peptides, e.g., peptide derivatives (for example, that contain one or more non-naturally occurring amino acids) can also be used. One example of these are peptoid libraries (Simon et al. (1992) *Proc. Natl. Acad. Sci. USA* 89: 9367-9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al. (1994) *Proc. Natl. Acad. Sci. USA* 91: 11138-11142).

The members of the libraries that can be screened according to the invention are not limited to the 20 naturally occurring amino acids. In particular, chemically synthesized libraries and polysome-based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid; 4-aminobutyric acid; 2-amino butyric acid; γ-Abu; ε-Ahx; 6-amino hexanoic acid; 2-amino isobutyric acid; 3-amino propionic acid; ornithine; norleucine; norvaline; hydroxyproline; sarcosine; citrulline; cysteic acid; t-butylglycine; t-butylalanine; phenylglycine; cyclohexylalanine; β-alanine; designer amino acids such as β-methyl amino acids; Cα-methyl amino acids; Nα-methyl amino acids; fluoro-amino acids; and the like. Furthermore, the natural and non-natural amino acids can be either D (dextrorotary) or L (levorotary).

The present invention also contemplates isolated nucleic acid molecules that encode the functionally equivalent peptides described herein, vectors, transformed or transfected host cells and methods of producing functionally equivalent peptides.

The peptides or the functionally equivalent peptides of the present invention are preferably conjugated to the carrier by chemical means. The peptides or the functionally equivalent peptides of the present invention can be conjugated to the carrier as a monomer, dimer, trimer or oligomer. The conjugation of peptides or the functionally equivalent peptides to an immunogenic carrier is described, for example, in Turpen et al. (1995) *Bio/Technology* 13: 53-57, which is incorporated herein by reference.

The peptides and conjugates of the present invention may be produced from an isolated HER-2/neu protein, synthetically produced, or genetically engineered and recombinantly produced. Automated synthetic production of peptides provides an alternate method for preparing the peptides and conjugates of the present invention. For example, any of the commercially available solid-phase techniques may be employed, such as the Merrifield solid phase synthesis method, in which amino acids are sequentially added to a growing amino acid chain. (See, Merrifield (1963) *J. Am. Chem. Soc.* 85: 2149-2146).

The transformed host cells of the present invention are cells which have been transformed or transfected with expression vectors constructed using recombinant DNA techniques and which contain isolated nucleic acid molecules encoding any peptide or conjugate of the present invention, as disclosed herein. Transformed host cells may express the desired peptide or conjugate but host cells transformed for purposes of cloning or amplifying the nucleic acid molecules of the present invention do not need to express the desired peptide or conjugate. Expressed peptides and conjugates will preferably be secreted into the culture supernatant.

Suitable host cells for expression of recombinant proteins include prokaryotes, yeast (members of Saccharomyces, such as *S. cerevisiae*, Pichia or Kluyveromyces or the like) or higher eukaryotic cells under the control of appropriate promoters. Prokaryotes include gram negative or gram positive organisms, for example *E. coli* or Bacilli. Suitable prokaryotic hosts for transformation include *E. coli, Bacillus subtilis, Salmonella typhimurium*, and various species within the genera Pseudomonas, Streptomyces, and Staphylococcus, although other hosts may also be employed. Higher eukaryotic cells include established cell lines of insect or mammalian origin as described below. Cell-free translation systems could also be employed to produce HER-2/neu polypeptides using RNAs derived from DNA constructs. Appropriate cloning and expression vectors for use with bacterial, fungal, yeast, and mammalian cellular hosts are described, for example, by Pouwels et al. (1985) *Cloning Vectors: A Laboratory Manual*, Elsevier, N.Y.

Various mammalian or insect (e.g., Spodoptera or Trichoplusia) cell culture systems can also be employed to express the recombinant peptides and conjugates of the present invention. Baculovirus systems for production of heterologous polypeptides in insect cells are disclosed by Luckow et al. (1988) *Bio/Technology* 6: 47. Examples of suitable mammalian host cell lines include the COS-7 lines of monkey kidney cells, described by Gluzman (*Cell* 23: 175 (1981)), and other cell lines capable of expressing an appropriate vector including, for example, CV-1/EBNA (ATCC CRL 10478), L cells, C127, 3T3, Chinese hamster ovary (CHO), COS, NS-1, HeLa and BHK cell lines.

The peptides and conjugates of the present invention, as described herein, may be isolated by physical, mechanical or chemical methods. The peptide or conjugate may be further purified by any number of techniques known in the art. For example, the peptides and conjugates may be prepared by culturing transformed or transfected host cells of the present invention and then purified from culture media or cell extracts by extraction, salting out, filtration or ultrafiltration, chromatography, including size exclusion, ion-exchange, normal-phase, reverse-phase, or affinity chromatography, or a combination thereof.

Recombinant expression vectors contain a DNA sequence encoding a HER-2/neu polypeptide operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation. An origin of replication and a selectable marker to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, in reading frame. DNA sequences encoding HER-2/neu polypeptides which are to be expressed in a microorganism will preferably contain no introns that could prematurely terminate transcription of DNA into mRNA.

Expression vectors for bacterial use may comprise a selectable marker and bacterial origin of replication derived from commercially available plasmids comprising genetic elements of the well known cloning vector pBR322 (ATCC 37017). Such commercial vectors include, for example, pKK223-3. These pBR322 "backbone" sections are combined with an appropriate promoter and the structural sequence to be expressed. *E. coli* is typically transformed using derivatives of pBR322, a plasmid derived from an *E. coli* species (Bolivar et al. (1977) *Gene* 2: 95). pBR322 contains genes for ampicillin and tetracycline resistance and thus provides simple means for identifying transformed cells.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258: 2674 (1982)) and Beier et al. (*Nature* 300: 724 (1982)). The yeast α-factor leader, which directs secretion of heterologous proteins, can be inserted between the promoter and the structural gene to be expressed (See, e.g., Kurjan et al. (1982) *Cell* 30: 933; and Bitter et al. (1984) *Proc. Natl. Acad. Sci. USA* 81: 5330). The leader sequence may be modified to contain, near its 3' end, one or more useful restriction sites to facilitate fusion of the leader sequence to foreign genes. The transcriptional and translational control sequences in expression vectors to be used in transforming vertebrate cells may be provided by viral sources. For example, commonly used promoters and enhancers are derived from polyoma, adenovirus 2, simian virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al. (1978) Nature 273: 113). Smaller or larger SV40 fragments may also be used, provided the approximately 250 bp sequence extending from the Hind III site toward the Bgl II site located in the viral origin of replication is included. Further, viral genomic promoter, control and/or signal sequences may be utilized, provided such control sequences are compatible with the host cell chosen. Exemplary vectors can be constructed as disclosed by Okayama et al. (1983) *Mol. Cell. Biol.* 3: 280.

Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Promoters commonly used in recombinant microbial expression vectors include the β-lactamase (penicillinase) and lactose promoter system (Chang et al. (1978) *Nature* 275: 615; and Goeddel et al. (1979) *Nature* 281: 544), the tryptophan (trp) promoter system (Goeddel et al. (1980) *Nucl. Acids Res.* 8: 4057; and European Patent Application 36,776) and the tac promoter (Maniatis (1982) *Molecular Cloning: A Laboratory Manual*, Cold Spring Harbor Laboratory, p. 412). A particularly useful bacterial expression system employs the phage $\lambda P_L$ promoter and cI857ts thermolabile repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al. (1980) *J. Biol. Chem.* 255: 2073) or other glycolytic enzymes (Hess et al. (1968) *J. Adv. Enzyme Reg.* 7: 149; and Holland et al. (1978) *Biochem.* 17: 4900), such as enolase, glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in European Patent Application 73,657.

Administration of any of the compositions of the present invention, as described herein, can induce continued expansion in the number of T cells necessary for therapeutic attack against cells in which the HER-2/neu oncogene is associated. The compositions of the present invention can be administered intravenously, subcutaneously, intraperitoneally, intramuscularly, or orally in capsule or pill form. Typically, about 0.01 µg/kg to about 100 mg/kg body weight will be administered by the intradermally, subcutaneously, intraperitoneally, intramuscularly, or intravenously. A preferred dosage is about 1 µg/kg to about 1 mg/kg, with about 5 µg/kg to about 200 µg/kg particularly preferred. It will be evident to those skilled in the art that the number and frequency of administration will be dependent upon the response of the patient. It may be desirable to administer the compositions of the present invention repetitively. It will be evident to those skilled in this art that more than one conjugate of the present invention, as described herein, may be administered either simultaneously or sequentially.

The conjugates of the present invention, as disclosed herein, are preferably formulated for use in the above methods as a pharmaceutical composition (e.g., vaccine). Compositions of the present invention comprise one or more conjugates in combination with a pharmaceutically acceptable carrier. As used herein, the term "pharmaceutically acceptable carrier" includes excipients, diluents, adjuvants and the like. Such carriers will be nontoxic to recipients at the dosages and concentrations employed. The present invention also contemplates compositions further comprising chemotherapeutic and/or other therapeutic agents.

Pharmaceutically acceptable carriers include delivery and immunostimulatory substances designed to enhance conjugate immunogenicity. Examples of vehicles for antigen delivery include aluminum salts, water-in-oil emulsions, biodegradable oil vehicles, oil-in-water emulsions, biodegradable microcapsules, and liposomes. Examples of immunostimulatory substances (adjuvants) include N-acetylmuramyl-L-alanine-D-isoglutamine (MDP), lipopolysaccharides (LPS), glucan, IL-12, GM-CSF, gamma interferon and IL-15.

While any pharmaceutically acceptable carrier known to those of ordinary skill in the art may be employed in the compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. The conjugates of the present invention may be encapsulated within the biodegradable microsphere or associated with the surface of the microsphere.

Pharmaceutically acceptable carriers include diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

Antibodies specific for HER-2/neu protein may be detected in a variety of biological fluids or tissues including sera and ascites using the peptides, or functionally equivalent peptides thereof, of the present invention. Briefly, a biological fluid or tissue sample is isolated from a warm-blooded animal, such as a human, for whom it is desired to determine whether antibodies specific for a HER-2/neu protein are present. The biological fluid or tissue is incubated with a peptide, or functionally equivalent peptides thereof, of the present invention under conditions sufficient to permit immunocomplexes to form between the polypeptide and antibodies specific for the protein. For example, a biological fluid or tissue and peptide or functionally equivalent peptides thereof, may be incubated at 4° C. for 24-48 hours. Following the incubation, the reaction mixture is tested for the presence of immunocomplexes. Detection of one or more immunocomplexes formed between a peptide and antibodies specific for HER-2/neu polypeptide may be accomplished by a variety of known techniques, such as radioimmunoassays (RIA) and enzyme-linked immunosorbent assays (ELISA).

Suitable immunoassays include the double-monoclonal-antibody sandwich-immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "Western blot" method of Gordon et al. (U.S. Pat. No. 4,452,901); immunoprecipitation of labeled ligand (Brown et al. (1980) *J. Biol. Chem.* 255: 4980-4983); enzyme-linked immunosorbent assays as described by, for example, Raines and Ross (*J. Biol. Chem.* 257: 5154-5160 (1982)); immunocytochemical techniques, including the use of fluorochromes (Brooks et al. (1980) *Clin. Exp. Immunol.* 39: 477); and neutralization of activity (Bowen-Pope et al. (1984) *Proc. Natl. Acad. Sci. USA* 81: 2396-2400), all of which are hereby incorporated by reference. In addition to the immunoassays described above, a number of other immunoassays are available, including those described in U.S. Pat. Nos.: 3,817,827; 3,850,752; 3,901,654; 3,935,074; 3,984,533; 3,996,345; 4,034,074; and 4,098,876, all of which are herein incorporated by reference.

For detection purposes, a peptide ("antigen") of the present invention, as described herein, may either be labeled or unlabeled. When unlabeled, the antigen finds use in agglutination assays. In addition, unlabeled antigen can be used in combination with labeled molecules that are reactive with immunocomplexes, or in combination with labeled antibodies (second antibodies) that are reactive with the antibody directed against the peptide of the present invention. Alternatively, the antigen can be directly labeled. Where it is labeled, the reporter group can include radioisotopes, fluorophores, enzymes, luminescers, or dye particles. These and other labels are well known in the art and are described, for example, in the following U.S. Pat Nos.: 3,766,162; 3,791,932; 3,817,837; 3,996,345; and 4,233,402.

Typically in an ELISA assay, antigen is adsorbed to the surface of a microtiter well. Residual protein-binding sites on the surface are then blocked with an appropriate agent, such as bovine serum albumin (BSA), heat-inactivated normal goat serum (NGS), or BLOTTO (buffered solution of nonfat dry milk which also contains a preservative, salts, and an antifoaming agent). The well is then incubated with a sample suspected of containing specific antibody. The sample can be applied neat, or, more often, it can be diluted, usually in a buffered solution which contains a small amount (0.1%-5.0% by weight) of protein, such as BSA, NGS, or BLOTTO. After incubating for a sufficient length of time to allow specific binding to occur, the well is washed to remove unbound protein and then incubated with an anti-species specific immunoglobulin antibody labeled with a reporter group. The reporter group can be chosen from a variety of enzymes, including horseradish peroxidase, beta-galactosidase, alkaline phosphatase, and glucose oxidase. Sufficient time is allowed for specific binding to occur, then the well is again washed to remove unbound antibody, and the substrate for the enzyme is added. Color is allowed to develop and the optical density of the contents of the well is determined visually or instrumentally.

In a related aspect of the invention, the detection of immunocomplexes formed between peptides of the present invention and antibodies in biological fluid or tissue which are specific for a HER-2/neu protein may be used to monitor the effectiveness of cancer therapy for a malignancy in which the HER-2/neu oncogene is associated. Samples of biological fluid or tissue taken from an individual prior to and subsequent to initiation of therapy may be analyzed for the immunocomplexes by the methodologies described above. Briefly, the number of immunocomplexes detected in both samples are compared. A substantial change in the number of immunocomplexes in the second sample (post-therapy initiation) relative to the first sample (pre-therapy) reflects successful therapy.

EXAMPLES

A. Production of Peptides and Conjugates

The peptides described by SEQ ID NO: 1 and 2 were produced and conjugated to keyhole limpet hemocyanin (KLH).

The peptides were synthesized by solid-phase synthesis according to he Fmoc protecting groups strategy. Conjugation was effected via the thio-function of the C-terminal cysteine to the maleimide-modified KLH.

B. Immunization

The first group of five mice (test group) were administered the two peptides (SEQ ID NO: 1 and 2), each conjugated to KLH and mixed with Gerbu adjuvant. Each injection contained 100 µg of each conjugate in a volume of 100 µl mixed with 100 µl of Gerbu adjuvant, for a total of 200 µl of antigen solution per injection. The second group of five mice (control group) were treated with 200 µl of a mixture of 100 µl of water with 100 µl of Gerbu adjuvant. The composition was administered subcutaneously into the knee fold of both groups. After the initial administration (priming), three additional administrations (boosters) were done at 3-week intervals. The animals were killed seven days after the last booster. Blood, spleen, liver, lung and kidneys were removed.

Gerbu adjuvant is an adjuvant formulation based on N-acetylgucosaminyl-N-acetylmuramyl-L-alanyl-D-isoglutamine, with dimethyldioctadecyl ammonium chloride and a zinc-L-proline complex as synergists. This adjuvant can be procured from Gerbu-Biotechnik GmbH, Gaiberg, Germany.

C. Detection of T-Cell Activation in a Proliferation Assay

Spleen cells obtained from five mice immunized with peptides described by SEQ ID NO: 1 and 2 were first stimulated with the peptides described by SEQ ID NO: 1 and 2. Cell proliferation is quantified by measuring the uptake of $^3$H thymidine (counts per minute (cpm)). Stimulation index (SI) refers to the quotient of cpm of cells stimulated with the particular peptide divided by cpm of unstimulated cells. In 96-well plates, $2\times10^5$ cells per well were incubated for five days with the two polypeptides (SEQ ID NO: 1 and 2) at a concentration of 20 µg/ml. After incubation [$^3$H] thymidine was added and the uptake of radioactivity was measured after an additional 18 hours of incubation.

The stimulation index in the immunized group of five mice (test group) varied from 1.0 to 1.6 for the peptide described by SEQ ID NO: 1 and from 1.5 to 2.0 for the peptide described by SEQ ID NO: 2. The stimulation index in the control group of five mice had the value 1.0 in all cases. No proliferation of cells was detected.

D. Detection of HER-2/neu-Specific Antibodies by Immunoprecipitation

Since there is no commercially available HER-2/neu protein, a cell lysate of SKBR-3 breast cancer cells overexpressing HER-2/neu was used. Mouse sera from either the control or test group were incubated with the cell lysate. If specific antibodies were present in the serum, HER-2/neu was precipitated from the cell lysate. The resultant immune complex can be isolated with the aid of protein A+G agarose (binding antibodies). These complexes were then separated by 6% polyacrylamide gel electrophoresis (PAGE) and transferred to a nitrocellulose membrane. Precipitated HER-2/neu was detected with the aid of a commercially available anti-HER-2/neu antibody (Zymed). The corresponding band is visualized on the membrane by staining (FIG. 1). Specific anti-HER-2/neu antibodies were detected in all sera of the test group. All sera of the control group clearly showed a negative result. The method described here serves as qualitative detection.

E. Detection of HER-2/neu-Specific Antibodies by ELISA

The wells of a 96-well ELISA plate were first coated with herceptin (anti-HER 2/neu antibody from Genentech Inc.). Non-specific binding sites were blocked using a 2% milk solution. The wells were then incubated with the membrane fractions from SKBR-3 cells overexpressing HER-2/neu protein. To quantify the non-specific background, control wells were incubated with membrane fractions of HTB132 cells not expressing HER-2/neu protein. In both cases, non-specific binding sites were then saturated (blocked) using a 2% milk solution.

The sera of the five immunized mice (test group) and those of the five mice of the control group were pipetted into the wells of a 96-well plate at a dilution of 1:100. For each test and control serum, two wells containing SKBR-3 membranes and two wells containing HTB132 membranes were used. If there are specific antibodies against HER-2/neu protein in the serum, they will bind to the antigen which can then be detected with horseradish peroxidase (HRP) that is coupled to secondary antibodies. HRP produces visible color upon reaction with a chromogenic substrate. The absorption at 450 nm is determined and corrected against the background at 650 nm (ODs). The difference between the OD of the two wells incubated with the SKBR-3 lysate, minus the OD of the two wells incubated with HTB132 lysate is assessed using serum from each test group. This method permits a comparison of the antibody titer in test and control sera, with increased OD corresponding to increased antibody titer.

Sera of all mice before and after vaccination were evaluated. A clear increase in OD after immunization was observed in 4 out of 5 mice of the test group. The OD obtained for the control group showed no change of antibody titer.

F. Histopathology

Lungs, liver and kidneys were examined histopathologically for autoimmune reactions. Organs were assessed as NAD in all cases.

---

We claim:

1. An isolated peptide as set forth in SEQ ID NO:1 or SEQ ID NO:2.

2. A conjugate comprising the peptide of claim 1 linked to an immunogenic carrier.

3. The conjugate of claim 2, wherein the immunogenic carrier is selected from the group consisting of key-hole limpet hemocyanin (KLH) and tetanus toxoid (TT).

4. A composition comprising the conjugate of claim 3 and a pharmaceutically acceptable carrier.

5. The conjugate of claim 2, wherein between 2 and 10 peptides are linked to the immunogenic carrier.

6. A composition comprising the conjugate of claim 5 and a pharmaceutically acceptable carrier.

7. A composition comprising the conjugate of claim 2 and a pharmaceutically acceptable carrier.

8. A method of eliciting or enhancing an immune response in a subject in need thereof comprising administering the composition of claim 7.

9. A method of detecting the presence of antibodies against the HER-2/neu protein comprising the steps of mixing a biological fluid or tissue obtained from a subject with the peptide of claim 1 and detecting the presence of antibodies by formation of a complex between the peptide and said antibodies.

10. A kit for detecting antibodies that specifically bind a HER-2/neu protein, wherein said kit comprises:
   a) a first container or containers comprising an isolated peptide as set forth in SEQ ID NO:1 or SEQ ID NO:2; and
   b) a second container containing buffers and factors.

* * * * *

UNITED STATES PATENT AND TRADEMARK OFFICE
Certificate

Patent No. 7,348,010 B2            Patented: March 25, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Christoph Zielinski, Vienna (AT); Otto Scheiner, Perchtoldsdort (AT) Erika Jensen-Jarolim, Vienna (AT); Heimo Breiteneder, Vienna (AT); Hubert Pehamberger, Vienna (AT); and Ursula Wiedermann, Vienna (AT).

Signed and Sealed this Nineteenth Day of July 2011.

GARY B. NICKOL
*Supervisory Patent Examiner*
Art Unit 1645
Tecnology Center 1600

SEQUENCE LISTING

```
<160> NUMBER OF SEQ ID NOS: 3

<210> SEQ ID NO 1
<211> LENGTH: 17
<212> TYPE: PRT
<213> ORGANISM: homo sapiens

<400> SEQUENCE: 1

Cys Arg Val Leu Gln Gly Leu Pro Arg Glu Tyr Val Asn Ala Arg His
1               5                   10                  15

Cys

<210> SEQ ID NO 2
<211> LENGTH: 14
<212> TYPE: PRT
<213> ORGANISM: homo sapiens

<400> SEQUENCE: 2

Tyr Met Pro Ile Trp Lys Phe Pro Asp Glu Glu Gly Ala Cys
1               5                   10

<210> SEQ ID NO 3
<211> LENGTH: 1255
<212> TYPE: PRT
<213> ORGANISM: homo sapiens
<220> FEATURE:
<221> NAME/KEY: DOMAIN
<222> LOCATION: (1)..(675)
<223> OTHER INFORMATION: Extracellular Domain

<400> SEQUENCE: 3

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45
```

-continued

```
Leu Tyr Gln Gly Cys Gln Val Gln Gly Asn Leu Glu Leu Thr Tyr
     50                  55                  60
Leu Pro Thr Asn Ala Ser Leu Ser Phe Leu Gln Asp Ile Gln Glu Val
 65                  70                  75                  80
Gln Gly Tyr Val Leu Ile Ala His Asn Gln Val Arg Gln Val Pro Leu
                 85                  90                  95
Gln Arg Leu Arg Ile Val Arg Gly Thr Gln Leu Phe Glu Asp Asn Tyr
             100                 105                 110
Ala Leu Ala Val Leu Asp Asn Gly Asp Pro Leu Asn Asn Thr Thr Pro
         115                 120                 125
Val Thr Gly Ala Ser Pro Gly Gly Leu Arg Glu Leu Gln Leu Arg Ser
     130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                 165                 170                 175
Asn Gln Leu Ala Leu Thr Leu Ile Asp Thr Asn Arg Ser Arg Ala Cys
             180                 185                 190
His Pro Cys Ser Pro Met Cys Lys Gly Ser Arg Cys Trp Gly Glu Ser
         195                 200                 205
Ser Glu Asp Cys Gln Ser Leu Thr Arg Thr Val Cys Ala Gly Gly Cys
     210                 215                 220
Ala Arg Cys Lys Gly Pro Leu Pro Thr Asp Cys Cys His Glu Gln Cys
225                 230                 235                 240
Ala Ala Gly Cys Thr Gly Pro Lys His Ser Asp Cys Leu Ala Cys Leu
                 245                 250                 255
His Phe Asn His Ser Gly Ile Cys Glu Leu His Cys Pro Ala Leu Val
             260                 265                 270
Thr Tyr Asn Thr Asp Thr Phe Glu Ser Met Pro Asn Pro Glu Gly Arg
         275                 280                 285
Tyr Thr Phe Gly Ala Ser Cys Val Thr Ala Cys Pro Tyr Asn Tyr Leu
     290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                 325                 330                 335
Pro Cys Ala Arg Val Cys Tyr Gly Leu Gly Met Glu His Leu Arg Glu
             340                 345                 350
Val Arg Ala Val Thr Ser Ala Asn Ile Gln Glu Phe Ala Gly Cys Lys
         355                 360                 365
Lys Ile Phe Gly Ser Leu Ala Phe Leu Pro Glu Ser Phe Asp Gly Asp
     370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                 405                 410                 415
Asp Ser Leu Pro Asp Leu Ser Val Phe Gln Asn Leu Gln Val Ile Arg
             420                 425                 430
Gly Arg Ile Leu His Asn Gly Ala Tyr Ser Leu Thr Leu Gln Gly Leu
         435                 440                 445
Gly Ile Ser Trp Leu Gly Leu Arg Ser Leu Arg Glu Leu Gly Ser Gly
     450                 455                 460
```

-continued

```
Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
        660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
        820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
```

-continued

```
               885                 890                 895
Arg Arg Phe Thr His Gln Ser Asp Val Trp Ser Tyr Gly Val Thr Val
           900                 905                 910

Trp Glu Leu Met Thr Phe Gly Ala Lys Pro Tyr Asp Gly Ile Pro Ala
           915                 920                 925

Arg Glu Ile Pro Asp Leu Leu Glu Lys Gly Glu Arg Leu Pro Gln Pro
           930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
               965                 970                 975

Ser Arg Met Ala Arg Asp Pro Gln Arg Phe Val Val Ile Gln Asn Glu
           980                 985                 990

Asp Leu Gly Pro Ala Ser Pro Leu Asp Ser Thr Phe Tyr Arg Ser Leu
           995                 1000                1005

Leu Glu Asp Asp Asp Met Gly Asp Leu Val Asp Ala Glu Glu Tyr
           1010                1015                1020

Leu Val Pro Gln Gln Gly Phe Phe Cys Pro Asp Pro Ala Pro Gly
           1025                1030                1035

Ala Gly Gly Met Val His His Arg His Arg Ser Ser Ser Thr Arg
           1040                1045                1050

Ser Gly Gly Gly Asp Leu Thr Leu Gly Leu Glu Pro Ser Glu Glu
           1055                1060                1065

Glu Ala Pro Arg Ser Pro Leu Ala Pro Ser Glu Gly Ala Gly Ser
           1070                1075                1080

Asp Val Phe Asp Gly Asp Leu Gly Met Gly Ala Ala Lys Gly Leu
           1085                1090                1095

Gln Ser Leu Pro Thr His Asp Pro Ser Pro Leu Gln Arg Tyr Ser
           1100                1105                1110

Glu Asp Pro Thr Val Pro Leu Pro Ser Glu Thr Asp Gly Tyr Val
           1115                1120                1125

Ala Pro Leu Thr Cys Ser Pro Gln Pro Glu Tyr Val Asn Gln Pro
           1130                1135                1140

Asp Val Arg Pro Gln Pro Pro Ser Pro Arg Glu Gly Pro Leu Pro
           1145                1150                1155

Ala Ala Arg Pro Ala Gly Ala Thr Leu Glu Arg Pro Lys Thr Leu
           1160                1165                1170

Ser Pro Gly Lys Asn Gly Val Val Lys Asp Val Phe Ala Phe Gly
           1175                1180                1185

Gly Ala Val Glu Asn Pro Glu Tyr Leu Thr Pro Gln Gly Gly Ala
           1190                1195                1200

Ala Pro Gln Pro His Pro Pro Ala Phe Ser Pro Ala Phe Asp
           1205                1210                1215

Asn Leu Tyr Tyr Trp Asp Gln Asp Pro Pro Glu Arg Gly Ala Pro
           1220                1225                1230

Pro Ser Thr Phe Lys Gly Thr Pro Thr Ala Glu Asn Pro Glu Tyr
           1235                1240                1245

Leu Gly Leu Asp Val Pro Val
           1250                1255
```